US006207827B1

(12) United States Patent
Guit

(10) Patent No.: US 6,207,827 B1
(45) Date of Patent: Mar. 27, 2001

(54) PROCESS TO SEPARATE ε-CAPROLACTAM FROM 6-AMINOCAPROAMIDE AND 6-AMINOCAPROAMIDE OLIGOMERS

(75) Inventor: Rudolf P. M. Guit, Maastricht (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/295,310

(22) Filed: Apr. 21, 1999

Related U.S. Application Data

(63) Continuation of application No. PCT/NL97/00033, filed on Feb. 5, 1997, and a continuation-in-part of application No. PCT/NL97/00467, filed on Aug. 14, 1997.

(30) Foreign Application Priority Data

Oct. 21, 1996 (NL) ..................... 96202931

(51) Int. Cl.[7] ..................... C07D 201/16
(52) U.S. Cl. ..................... 540/540
(58) Field of Search ..................... 540/540

(56) References Cited

U.S. PATENT DOCUMENTS 4,314,940 * 2/1982 Senni et al. ..................... 260/293.3
4,730,040 3/1988 Vagt et al. ..................... 540/538
5,495,016 2/1996 Achhammer et al. ..................... 540/539

FOREIGN PATENT DOCUMENTS 0 729 944 A2 9/1996 (EP) .
WO 97/30028 8/1997 (WO) .

OTHER PUBLICATIONS

Abstract of JP 53050189, May 1978.*
Abstract of NL 6803152, 1968.*

* cited by examiner

*Primary Examiner*—Bruck Kifle
(74) *Attorney, Agent, or Firm*—Pillsbury Winthrop LLP

(57) ABSTRACT

Process to separate ε-caprolactam from 6-aminocaproamide and 6-aminocaproamide oligomers, wherein ε-caprolactam, 6-aminocaproamide and 6 aminocaproamide oligomers are present in a first aqueous starting mixture, which mixture is contacted with an alcohol extraction solvent, resulting in a first aqueous raffinate phase which is poor in ε-caprolactam and an alcohol phase which is rich in ε-caprolactam and which alcohol phase contains 6-aminocaproamide and/or 6-aminocaproamide oligomers, wherein the latter alcohol phase is subsequently contacted with water (backwash water) resulting in an alcohol extract phase poor in 6-aminocaproamide and/or 6-aminocaproamide oligomers and a second aqueous raffinate phase rich in 6-aminocaproamide and/or 6-aminocaproamide oligomers.

9 Claims, 1 Drawing Sheet

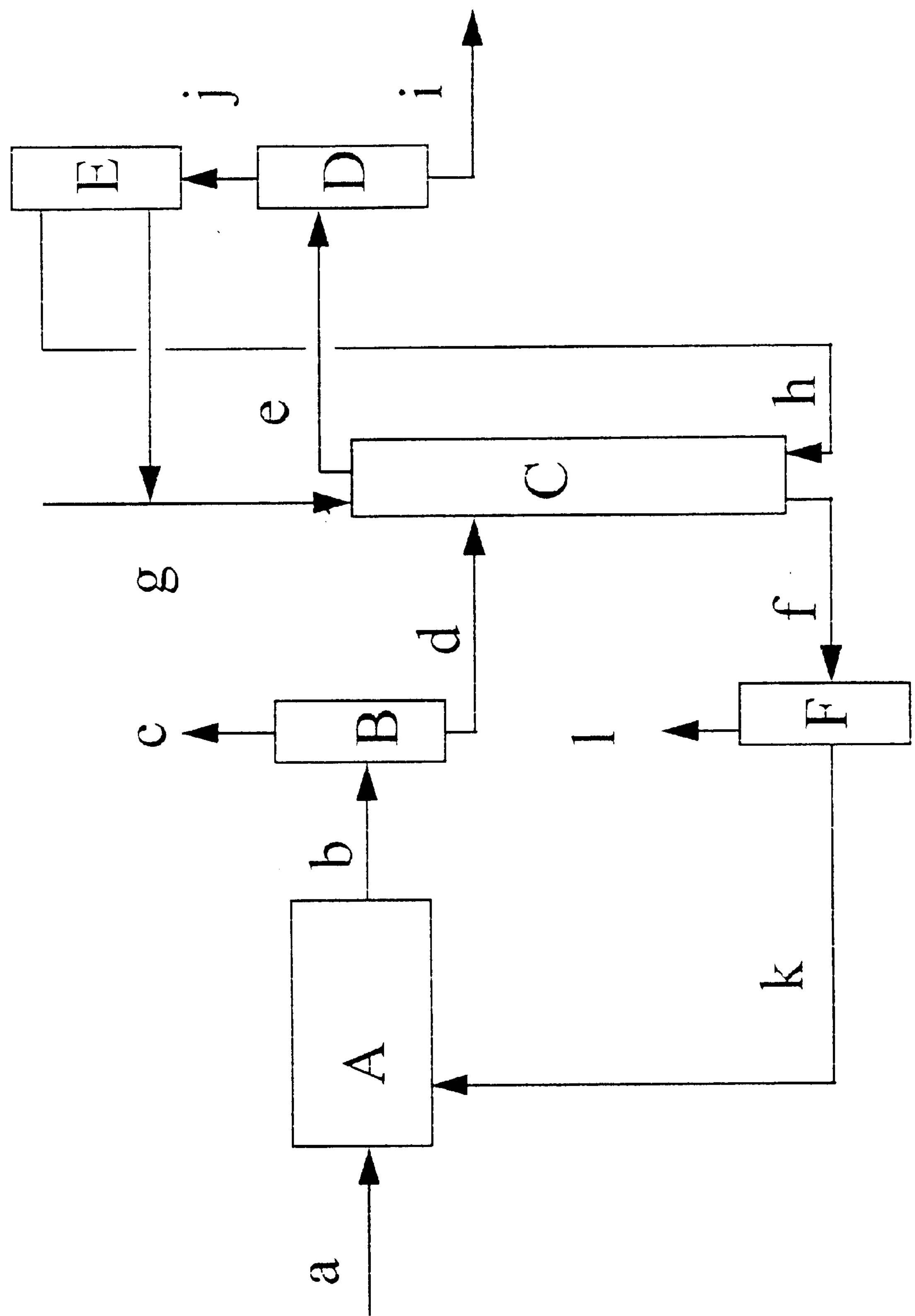
A
B
C
D
E
F
a
b
c
d
e
f
g
h
i
j
k
l

PROCESS TO SEPARATE ϵ-CAPROLACTAM FROM 6-AMINOCAPROAMIDE AND 6-AMINOCAPROAMIDE OLIGOMERS

This is a continuation of International Application No. PCT/NL97/00033 filed on Feb. 5, 1997 which designates the US and of International Application No. PCT/NL97/00467 filed on Aug.14, 1997.

The invention relates to a process to separate ϵ-caprolactam from 6-aminocaproamide and 6-aminocaproamide oligomers.

Such a process is known from U.S. Pat. No. 5495016. This patent publication describes a separation of ϵ-caprolactam from its nylon-6 oligomers by distillation.

A disadvantage of distillation is that ϵ-caprolactam will partly convert to more oligomers (2 wt. % absolute according to Example 1 of U.S. Pat. No. 5495016). Another disadvantage is fouling of pipes and other process equipment because of solidification of the oligomers present in the distillation residue.

The object of the present invention is to provide a method to separate ϵ-caprolactam from 6-aminocaproamide and its oligomers in which no ϵ-caprolactam is lost.

The object is achieved in that ϵ-caprolactam, 6-aminocaproamide and 6-aminocaproamide oligomers are present in a first aqueous starting mixture, which mixture is contacted with an alcohol extraction solvent, resulting in a first aqueous raffinate phase which is poor in ϵ-caprolactam and an alcohol phase which is rich in ϵ-caprolactam and which alcohol phase contains 6-aminocaproamide and/or 6-aminocaproamide oligomers, wherein the latter alcohol phase is subsequently contacted with water (backwash water) resulting in an alcohol extract phase poor in 6-aminocaproamide and/or 6-aminocaproamide oligomers and a second aqueous raffinate phase rich in 6-aminocaproamide and/or 6-aminocaproamide oligomers.

It has been found that by performing the process according the invention ϵ-caprolactam can be succesfully separated from 6-aminocaproamide and 6-aminocaproamide EP-A-729944 describes that ϵcaprolactam may be recovered from aqueous mixtures containing also oligomers of 6-aminocaproamide by extraction using methylene chloride, cyclohexane, toluene, benzene, chloroform or trichloroethane. This patent publication does not teach alcohol solvents as extraction agents. It has been found that the most promising extraction solvents of EP-A-729944 are the exemplified chloronated solvents. These solvents are however preferably not used because of environmental reasons.

NL-A-6803152 describes experiments of an extraction of ϵ-caprolactam from an aqueous mixture using a $C_4$–$C_8$ (cyclo)aliphatic alcohol solvent. This patent publication does not describe the presence of 6-aminocaproamide or its oligomer in the aqueous mixture. Furthermore no second extraction using water is described.

The first aqueous starting mixture may also contain 6-aminocaproic acid and 6-aminocaproic acid oligomers. Such mixtures are, for example, obtained in the process of EP-A-729944. It has been found that these compounds are also effectively separated from ϵ-caprolactam when performing the process according to the invention.

The oligomers are generally dimers and trimers of 6-aminocaproic acid or of 6-aminocaproamide. Higher oligomers can be present in a much lower content.

The concentration oligomers in the first aqueous mixture is preferably higher than 0.5 wt. %. More preferably not more than 10 wt. %.

The concentration of ϵ-caprolactam, 6minocaproic acid, 6-aminocaproamide and oligomers in the first aqueous mixture is preferably between 5–50 wt. % and more preferably between 10–35 wt. %. The concentration of ϵ-caprolactam is preferably between 5–30 wt. %. The concentration of 6-aminocaproamide is preferably between 0.1 and 10 wt. %. The concentration of 6-aminocaproic acid is preferably between 0.1 and 10 wt. %.

The alcohol extraction solvent is preferably a solvent which is substantially immiscible with the first aqueous mixture. By substantially immiscible is here meant that the mixture of alcohol solvent and the aqueous mixture results in two segregated phases at the extraction temperature. Preferable the mutual solubility under the conditions of the extraction is not higher than 30 wt. % and more preferably less than 20 wt. %.

The alcohol extraction solvent is preferably an aliphatic or cycloaliphatic compound having one or more hydroxyl groups. Such alcohols have preferably 4–12 carbon atoms and more preferably 5–8 carbon atoms. Preferably one or two and more preferably only one hydroxyl group is present. Preferably hindered alcohols are used. A hindered alcohol is a compound in which the hydroxyl group is bonded to a —$CR^1R^2R^3$ in which $R^1$ and $R^2$ are alkyl groups and $R^3$ is an alkyl group or hydrogen. This is advantageous in a process in which the resulting aqueous phases are used as feed to prepare ϵ-caprolactam. Hindered alcohols are less susceptible to react to N-alkylation products of ϵ-caprolactam.

Examples of compounds having two hydroxyl groups are hexanediol, nonanediol, neopentylglycol, methyl-methylpropanediol, ethyl-methylpropanediol or butyl-methylpropanediol. Examples of compounds having one hydroxyl group are cyclohexanol, n-butanol, n-pentanol, 2-pentanol, n-hexanol, 4-methyl-2-pentanol, 2-ethyl-1-hexanol, 2-propyl-1-heptanol, n-octanol, iso-nonylalcohol, n-decylalcohol and mixtures of linear and branched $C_8$-alcohols, mixtures of linear and branched $C_9$-alcohols and mixtures of linear and branched $C_{10}$-alcohols. Mixtures of the above mentioned alcohols can also be used. Preferred alcohols have a high affinity for ϵ-caprolactam, a lower boiling point than ϵ-caprolactam, a large density difference with water, commercially available, low mutual solubility with water and/or are biodegradable.

The back wash water may be pure water or water contaminated with other compounds, for example the alcohol compound. Preferably the water used is at least 95 wt. % pure water.

The first and second aqueous raffinate phases may be combined to form one aqueous mixture which can be used further. Preferably the first aqueous raffinate phase is combined with the aqueous starting mixture. Such a preferred embodiment of the process is preferably performed continuously in one process apparatus. This embodiment is characterized in that the extraction is performed in a vertically positioned vessel, wherein the aqueous starting mixture is fed at an intermediate position along the vessel, the alcohol extraction solvent is fed to the bottom of the vessel and the backwash water is fed to the top of the vessel, and in which the resulting aqueous raffinate and alcohol extract phases are obtained at the bottom and the top of the vessel respectively.

The amount of alcohol extraction solvent- and backwash water will depend on the partitioning coefficient of the components to be separated, which can be easily determined by one skilled in the art.

The extraction step is carried out at a temperature which is high enough in order to avoid precipitation of oligomers. The temperature of extraction can be generally between room temperature and 200° C. and is preferably between 20 and 170° C. Temperatures between 50 and 130° C. are even more preferred.

The pressure during the extraction step is not critical and can be, for example, between about 0.1 MPa and about 2.0 MPa, and preferably, between about 0.1 MPa and about 0.5 MPa. The pressure must be sufficient to maintain liquid phases during extraction.

The extraction can be carried out in well known extraction apparatuses, for example a counter current column, a series of mixer settlers, rotating disc contactors or pulsed packed columns.

The extraction step preferably yields a ε-caprolactam-containing alcohol phase which may contain between 10–40 wt. % ε-caprolactam.

After the extraction ε-caprolactam may be recovered from the alcohol phase by known separation methods, for example distillation and extraction. Preferably distillation is used in which the lower boiling alcohol and any water present in the alcohol phase is distilled from the ε-caprolactam. The alcohol solvent and water thus obtained is preferably reused in the extraction according to the invention.

The invention relates especially to the separation of ε-caprolactam from aqueous mixtures obtained in (I) a process to prepare ε-caprolactam in which 6-aminocapronitrile is converted into crude ε-caprolactam by reaction with water as described in for example U.S. Pat. No. 5495016, (II) a process to prepare ε-caprolactam by cyclization of 6-aminocaproic acid in water as described in for example U.S. Pat. No. 4730040 or (III) in which the starting mixture comprises 6-aminocaproic acid and 6-aminocaproamide as for example described in EP-A-729944.

The aqueous mixture obtained in processes (I) and (II) will also contain ammonia which is a side-product of the reaction to ε-caprolactam starting from 6-aminocapronitrile or 6-aminocaproamide. It is advantageous to separate the ammonia prior to the extraction, for example by distillation or steam stripping. In the distillation any unconverted 6-aminocapronitrile (in process (I)) and part of the water will generally be separated as well. The concentration of the ε-caprolactam, optionally 6-aminocaproic acid, optionally 6-aminocaproamide and oligomers in the aqueous mixture obtained after such an ammonia separation will be preferably higher than 10 wt%.

The reaction to ε-caprolactam can be performed continuously. The aqueous mixture obtained in the extraction according to the invention is preferably recycled to the cyclization processes as (I), (II) and (III) here above described. It has been found that the compounds, for example 6-aminocaproic acid, 6-aminocaproamide and oligomers which are present in this mixture can react to ε-caprolactam in a high yield. Thus by using extraction to isolate ε-caprolactam a valuable recycle stream is also obtained which can be succesfully used to prepare more ε-caprolactam. Preferably any alcohol solvent present in the aqueous phase is separated before the aqueous mixture is recycled to the cyclization reactor zone. Such a separation is preferably performed by distillation and more preferably by steam distillation.

In a preferred embodiment to prepare ε-caprolactam the following steps are performed:

(i) an aqueous mixture containing 6-aminocaproic acid, 6-aminocaproamide and their respective oligomers are reacted in the liquid phase to ε-caprolactam at a temperature of between 270 and 350° C. in a reaction zone.

(ii) ammonia is separated from the resulting aqueous mixture to a concentration of below 0.1 wt. %, (iii) ε-caprolactam is extracted from the aqueous mixture obtained in step (ii) by the process according to the invention resulting in an aqueous raffinate phase and an alcohol extract phase (iv) the aqueous raffinate phase is contacted with steam to separate any dissolved alcohol solvent from the aqueous raffinate phase (v) the aqueous phase obtained in step (iv) is recycled in step (i)

(vi) ε-caprolactam is separated from the alcohol phase and the resulting alcohol solvent is reused in step (iii).

The temperature in step (i) is preferably between 270 and 350° C., more preferably higher than 290°C. The pressure in step (i) is preferably between 5.0 and 20 MPa. Normally the pressure will be greater than or equal to the resulting pressure of the liquid reaction mixture and the temperature employed.

An example of a possible process scheme of the above embodiment is described in FIG. 1. In FIG. 1 it can be seen that an aqueous starting feed (a) is fed to cyclization reactor (A). Ammonia (c) is separated from aqueous reactor effluent (b) in distillation (B). The resulting aqueous liquid mixture (d) containing ε-caprolactam, 6-aminocaproic acid, 6-aminocaproamide and their respective oligomers is fed to extraction column (C). To this column a backwash water feed (g) and an alcohol solvent feed (h) is also fed. Resulting alcohol extract phase (e) is fed to a distillation column (D) in which the lower boiling alcohol and dissolved water is separated via (j) from ε-caprolactam product (i). In a liquid/liquid separator (E) the alcohol is separated from water, resulting in backwash water (g) (containing optionally some alcohol) and an alcohol solvent stream (h) (containing optionally some dissolved water). The aqueous raffinate phase (f) is fed to a steam stripper (F) in which any alcohol and any surplus water present in (f) is separated via (1). The resulting aqueous mixture (k) containing 6-aminocaproic acid, 6-aminocaproamide, their oligomers and optionally a small amount of ε-caprolactam is recycled to the reactor (A).

The inventions will now be elucidated by means of the following non-restrictive examples. The partition coefficient is defined as the quotient of the concentration (in wt. %) in the alcohol extract phase and the concentration (in wt. %) in the aqueous raffinate phase of a certain compound.

Example I 100 g of an aqueous mixture containing 15.5 wt. % ε-caprolactam, 5.2 wt. % 6-aminocaproic acid, 17.4 wt. % 6-aminocaproamide and 2.2 wt. % oligomers of 6-aminocaproic acid and 3.4 wt. % oligomers of 6-aminocaproamide was mixed well, long enough to reach equilibrium, with 100 g of 4-methyl-2-pentanol at 80° C.

The partition coefficient of ε-caprolactam was 3.3. No detectable amounts of 6-aminocaproic acid and oligomers of 6-aminocaproic acid were found in the alcohol phase. The partition coefficient of 6-amino-caproamide was 0.45 and of oligomer of 6-aminocaproamide-amide was 0.66.

Example II

To a vertical placed pulsed packed extraction column (diameter 2.5 cm) packed with 3 m of glass rashig rings (6 mm) an aqueous product feed was fed 1 m below the top, back-wash water was fed at 60° C. to the top and 4-methyl-2-pentanol was fed to the bottom at a rate:

| | |
|---|---|
| aqueous product feed | 1.65 kg/hr |
| back-wash water | 0.31 kg/hr |
| 4-methyl-2-pentanol | 1.10 kg/hr |

The composition was:

aqueous product feed 18.1 wt. % caprolactam 1.28 wt. % 6-aminocaproic acid (6ACA)

0.73 wt. % 6-aminocaproamide (6ACAM)

2.89 wt. % oligomers of 6ACA and 6ACAM.

At the top an alcohol phase (about 15 wt. % water) was obtained having a composition of 19.1 wt. % caprolactam (99.6% yield) <0.01 wt. % 6-aminocaproic acid <0.01 wt. % 6-aminoacproamide <0.01 wt. % oligomers The loss of 6-aminocaproamide, 6-aminocaproic acid and oligomers to the alcohol phase was less than 1% .

The ϵ-caprolactam still present in the resulting aqueous phase should not be considered as a loss when this mixture is reused in a process in which the 6 ACA, 6 ACAM and oligomers are converted to ϵ-caprolactam.

What is claimed is:

1. Process to separate ϵ-caprolactam from 6-aminocaproamide and 6-aminocaproamide oligomers, characterized in that ϵ-caprolactam, 6-aminocaproamide and 6-aminocaproamide oligomers are present in a first aqueous starting mixture, which mixture is contacted with an alcohol extraction solvent, resulting in a first aqueous raffinate phase which is poor in ϵ-caprolactam and an alcohol phase which is rich in ϵ-caprolactam and which alcohol phase contains 6-aminocaproamide and/or 6-aminocaproamide oligomers, wherein the latter alcohol phase is subsequently contacted with water (backwash water) resulting in an alcohol extract phase poor in 6-aminocaproamide and/or 6-aminocaproamide oligomers and a second aqueous raffinate phase rich in 6-aminocaproamide and/or 6-aminocaproamide oligomers.

2. Process according to claim 1, characterized in that the alcohol extraction solvent is a mono-alcohol having 5–8 carbon atoms.

3. Process according to claim 2, characterized in that the mono-alcohol is a hindered alcohol.

4. Process according to claim 3, characterized in that the alcohol is 4-methyl-2-pentanol.

5. Process according to any one of claims 1–4, characterized in that 6-aminocaproic acid and/or 6-aminocaproic acid oligomers are also present in the first aqueous starting mixture.

6. Process according to any one of claims 1–5, characterized in that the first aqueous starting mixture contans between 0.5–10 wt. % oligomers, between 5–30 wt. % ϵ-caprolactam, betweem 0.1 –10 wt. % 6-aminocaproic acid and between 0.1–10 wt. % 6-aminocaproamide.

7. Process according to any one of claims 1–6, characterized in that the temperature is between 50–130° C.

8. Process according to any one of claims 1–7, characterized in that the extraction is performed continuously and in which the first aqueous raffinate is combined with the first aqueous starting mixture.

9. Process according to claim 8, characterized in that the process is performed in a vertically positioned vessel, wherein the aqueous starting mixture is fed at an intermediate position along the vessel, the alcohol extraction solvent is fed to the bottom of the vessel and the backwash water is fed to the top of the vessel and in which the resulting aqueous raffinate and alcohol extract phases are obtained at the bottom and top of the vessel respectively.

* * * * *

UNITED STATES PATENT AND TRADEMARK OFFICE

CERTIFICATE OF CORRECTION

PATENT NO. : 6,207,827 B1
DATED : March 27, 2001
INVENTOR(S) : Guit

It is certified that error appears in the above-identified patent and that said Letters Patent is hereby corrected as shown below:

Title page,
Please change: "[73] Assignee: DSM N.V., Heerlen, Netherlands" to
-- [73] Assignee: DSM N.V., Heerlen, Netherlands and I.E. DU PONT DE NEMOURS AND COMPANY, Wilmington, Delaware, US Signed and Sealed this Fourth Day of September, 2001

*Attest:*

Nicholas P. Godici

NICHOLAS P. GODICI

*Attesting Officer* *Acting Director of the United States Patent and Trademark Office*